United States Patent [19]

Kobrehel et al.

[11] Patent Number: 5,250,518
[45] Date of Patent: Oct. 5, 1993

[54] O-METHYL DERIVATIVES OF AZITHROMYCIN A

[75] Inventors: Gabrijela Kobrehel, Slobodan Djokić; Gorjana Lazarevski, all of Zagreb, Yugoslavia

[73] Assignee: Pliva Farmaceutska, Kemijska, Prehrambena I Kozmeticka, Yugoslavia

[21] Appl. No.: 731,781

[22] Filed: Jul. 18, 1991

[30] Foreign Application Priority Data

Jul. 18, 1990 [YU] Yugoslavia .................. 1409/90

[51] Int. Cl.$^5$ .................... C07H 17/08; A61K 31/70
[52] U.S. Cl. ...................... 514/29; 536/7.2; 536/7.4
[58] Field of Search ............... 536/7.2, 7.4; 514/29

[56] References Cited

U.S. PATENT DOCUMENTS

| | | | |
|---|---|---|---|
| 4,474,768 | 10/1984 | Bright | 536/7.4 |
| 4,680,386 | 7/1987 | Morimoto et al. | 536/7.4 |
| 4,743,593 | 5/1988 | Hunt | 514/29 |
| 4,833,236 | 5/1989 | Morimoto et al. | 536/7.2 |

Primary Examiner—Johnnie R. Brown
Assistant Examiner—Elli Peselev
Attorney, Agent, or Firm—Pollock, Vande Sande & Priddy

[57] ABSTRACT

The invention relates to O-methyl derivatives of azithromycin A of the formula (I)

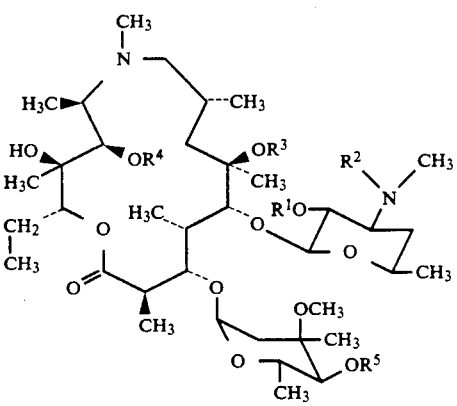

wherein
Ia $R^1=R^2=CO_2CH_2C_6H_5$, $R^3=CH_3$, $R^4=R^5=H$
Ib $R^1=R^2=CO_2CH_2C_6H_5$, $R^3=R^4=CH_3$, $R^5=H$
Ic $R^1=R^2=CO_2CH_2C_6H_5$, $R^3=R^5=H$, $R^4=C_3$
Id $R^1=R^2=CO_2CH_2C_6H_5$, $R^3=R^4=R^5=CH_3$
Ie $R^1=R^2=R^4=R^5=H$, $R^3=CH_3$
If $R^1=R^2=R^5=H$, $R^3=R^4=CH_3$
Ig $R^1=R^2=R^3=R^5=H$, $R^4=CH_3$
Ih $R^1=R^2=H$, $R^3=R^4=R^5=CH_3$
Ii $R^1=R^4=R^5=H$, $R^2=R^3=CH_3$
Ij $R^1=R^5=H$, $R^2=R^3=R^4=CH_3$
Ik $R^1=R^3=R^5=H$, $R^2=R^4=CH_3$
Il $R^1=H$, $R^2=R^3=R^4=R^5=CH_3$ to their pharmaceutically acceptable addition salts with inorganic or organic acids, to a process for their preparation and to their use in the obtaining of antibacterial pharmaceutical preparations.

4 Claims, No Drawings

O-METHYL DERIVATIVES OF AZITHROMYCIN A

This invention relates to novel, semisynthetic macrolide antibiotics of the azalide series, particularly to O-methyl derivatives of azithromycin A and to pharmaceutically acceptable addition salts thereof, to a process and intermediates for the preparation thereof, and to their use in the preparation of pharmaceuticals, which are particularly indicated as antimicrobial agents.

Erythromycin A is a macrolide antibiotic, whose structure is characterized by a 14-membered aglicone ring, possessing a keto group in C-9 position (Bunch R. L. et al, U.S. Pat. No. 2,653,899; September, 1953); it has been hitherto the leading macrolide antibiotic in the treatment of infections in humans. However, in acidic medium it is easily converted into anhydroerythromycin, which is an inactive C-6/C-12 metabolite of a spiroketal structure (Kurath P et al., Experientia 1971, 27 362). It has been known that the spiro-cyclisation of erythromycin A is successfully inhibited by means of a chemical transformation of C-9(S) and C-9(R) ketones upon the obtaining of C-9 oximes (Djokić S. et al., Tetrahedron Lett., 1967, 1945) or C-9(R) amines (Egan R. S. et al, J.Org.Chem., 1974, 39, 2492), or by the elimination of the C-9 ketone upon the expansion of the aglycone ring (Kobrehel G. et al., U.S. Pat. No. 4,328,334; May, 1982). Thus Beckmann rearrangement of erythromycin A oxime, followed by the reduction of the obtained imino ether (Djokić S. et al., J.Chem.Soc.Perkin Trans 1, 1986, 1881) yielded the 11-aza-10-deoxo-10-dihydroerythomycin A (9-deoxo-9a-aza-9a-homoerythromycin A), which was the first 15-membered macrolide antibiotic of the azalide series. Upon methylation of the newly introduced secondary amino group in the aglycone ring with formaldehyde in the presence of formic acid via the modified Eschweiler-Clark procedure (Kobrehel G. and Djokić S., BE patent 892,357; July, 1982), or upon preliminary protection of the amino groups by means of conversion into the corresponding N-oxides, followed by the alkylation and reduction of the obtained N-oxides (Bright G., U.S. Pat. No. 4,474,768; October, 1984), there was obtained the N-methyl-11-aza-10-deoxo-10-dihydroerythromycin A (9-deoxo-9a-aza-9a-methyl-9a-homoerythromycin A) (IUPAC Nomenclature of Organic Chemistry, 1979, 68-70. 459, 500-503), which is being clinically tested under the non-proprietary name of azithromycin. In comparison with the parent antbiotic, azithromycin exhibits, in addition to an improved stability in acidic medium, also an improved in vitro activity against gram-negative microorganisms and a significantly higher conncentration in the tissues, and there is even being tested the possibility of a one-day dose (Ratshema J. et al, Antimicrob. Agents Chemother., 1987, 31, 1939).

Further, it has been known that the C-6/C-12 spiro-cyclisation of erythromycin A is successfully inhibited by means of O-methylation of the hydroxy group in C-6 position of the aglycone ring (Watanabe Y. et al., U.S. Pat. No. 4,331,803; May, 1982). The reaction of erythromycin A with benzyl chloroformate, followed by the methylation of the obtained 2'-0,3'-N-bis(benzyloxycarbonyl)-derivative, upon the elimination of the protective groups in positions 2'- and 3'- as well as the N-methylation of the 3'-methylamino group under reductive conditions, yields, in addition to 6-O-methylerythromycin A, also significant quantities of 11-O-methyl- and 6,11-di-O-methylerythromycin A (Morimoto S. et al, J. Antibiotics 1984, 37, 187). A higher selectivity is achieved by the preliminary oximation of the C-9 ketones and the O-methylation of the corresponding substituted or unsubstituted benzyloximino derivatives (Morimoto S. et al, U.S. Pat. No. 4,680,368; July, 1987). 6-O-methyl-erythromycin A is being clinically tested under the non-proprietary name of clarithromycin. In comparison to erythromycin A, clarithromycin exhibits an improved in vitro activity against gram-positive microorganisms (Kirist H. A. et al, Antimicrobial Agents and Chemother., 1989,1419).

The Applicant's search has revealed no disclosure on O-methyl derivatives of azithromycin A in the State of the Art.

Hence the first object of the present invention are new O-methyl derivatives of azithromycin A of the formula (I)

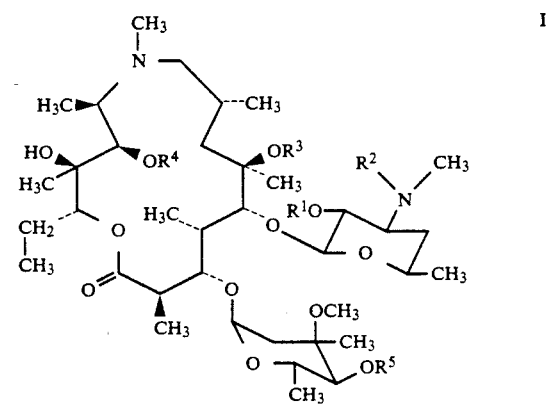

wherein

Ia $R^1=R^2=CO_2CH_2C_6H_5$, $R^3=CH_3$, $R^4=R^5=H$
Ib $R^1=R^2=CO_2CH_2C_6H_5$, $R^3=R^4=CH_3$, $R^5=H$
Ic $R^1=R^2=CO_2CH_2C_6H_5$, $R^3=R^5=H$, $R^4=C_3$
Id $R^1=R^2=CO_2CH_2C_6H_5$, $R^3=R^4=R^5=CH_3$
Ie $R^1=R^2=R^4=R^5=H$, $R^3=CH_3$
If $R^1=R^2=R^5=H$, $R^3=R^4=CH_3$
Ig $R^1=R^2=R^3=R^5=H$, $R^4=CH_3$
Ih $R^1=R^2=H$, $R^3=R^4=R^5=CH_3$
Ii $R^1=R^4=R^5=H$, $R^2=R^3=CH_3$
Ij $R^1=R^5=H$, $R^2=R^3=R^4=CH_3$
Ik $R^1=R^3=R^5=H$, $R^2=R^4=CH_3$
Il $R^1=H$, $R^2=R^3=R^4=R^5=CH_3$ and their pharmaceutically acceptable acid addition salts.

A further object of the present invention is a process for the preparation of O-methyl derivatives of azithromycin A of the formula (I) and of their pharmaceutically acceptable acid addition salts, wherein azithromycin or its dihydrate (Djokić S. et al., J. Chem. Research (S), 1988, 152-153; (M) 1988 1239-12621) of the formula (II)

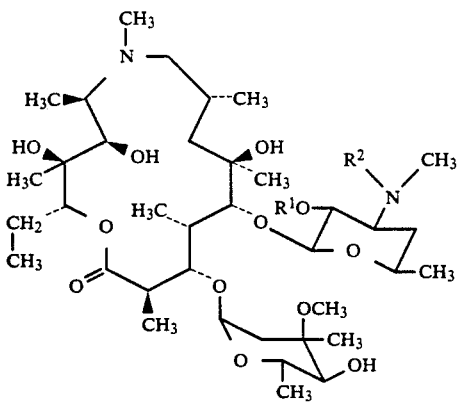

II wherein

IIa $R^1=H$, $R^2=CH_3$, is reacted with benzyl chloroformate in the presence of an excess of a suitable base, e.g. sodium hydrogen carbonate, in a reaction inert solvent, e.g. benzene, at a temperature of 25° C. to 60° C., within 3 to 24 hours, depending on the reaction temperature, followed by O-methylation of the hydroxy groups in the C-6, C-11 and C-4" positions of a new, as yet undisclosed intermediate 2'-O,3'-N-bis-(benzyloxycarbonyl)-N-demethyl-azithromycin A of the formula (II), wherein IIb $R^1=R^2=CO_2CH_2C_6H_5$, with a 1-18 molar excess of an appropriate methylation agent, e.g. methyl iodide, dimethyl sulfate, methyl methanesulfonate or methyl p-toluenesulfonate, in the presence of an appropriate base, e.g. sodium hydride, aqueous potassium hydroxide or sodium hydroxide, in an appropriate solvent, e.g. dimethyl sulfoxide or N,N-dimethyl-formamide, or their mixtures with a reaction inert solvent, e.g. tetrahydrofurane, acetonitrile, ethyl acetate, 1,2-dimethoxyethane, at a temperature of 0° C. to room temperature, within 3 to 30 hours, yielding a mixture of O-methyl-2'-O,3'-N-bis-(benzyloxycarbonyl)-N-demethyl-azithromycin A of the formula (I), wherein Ia $R^1=R^2=CO_2CH_2C_6H_5$, $R^3=CH_3$, $R^4=R^5=H$
Ib $R^1=R^2=CO_2CH_2C_6H_5$, $R^3=R^4=CH_3$, $R^5=H$
Ic $R^1=R^2=CO_2CH_2C_6H_5$, $R^3=R^5=H$, $R^4=C_3$
Id $R^1=R^2=CO_2CH_2C_6H_5$, $R^3=R^4=R^5=CH_3$ which is optionally subjected to A) separation on a silica gel column (Silica gel 60, Merck Co., 70-230 mesh) with the solvent system $CH_2Cl_2/CH_3OH/NH_4OH$ (90:9:0.5), yielding chromatographically homogenous compounds (Ia) of an $R_f$ 0.660, (Ib) of an $R_f$ 0.811, (Ic) of an $R_f$ 0.843 and (Id) of an $R_f$ 0.881, which are subsequently subjected to the elimination of the protecting benzyloxycarbonyl groups in positions 2'- and 3'- by means of hydrogenolysis in a solution of lower alcohols, e.g. methanol or ethanol, in the presence of a catalyst, e.g. palladium black or palladium-on-carbon, in a hydrogen atmosphere at a pressure of 1-20 bar, under stirring of the reaction mixture, within 2-10 hours, at room temperature, yielding, upon filtration of the catalyst and the isolation of the product by means of conventional ph-gradient extraction methods (pH 5.0 and pH 9.0) from water with an appropriate hydrophobic solvent, e.g. chloroform, dichloromethane, ethyl acetate etc., the O-methyl-N-demethyl-azithromycin A derivatives of formula (I), wherein Ie $R^1=R^2=R^4=R^5=H$, $R^3=CH_3$
If $R^1=R^2=R^5=H$, $R^3=R^4=CH_3$
Ig $R^1=R^2=R^3=R^5=H$, $R^4=CH_3$
Ih $R^1=R^2=H$, $R^3=R^4=R^5=CH_3$ which are then subjected to reductive N-methylation of the 3'-methylamino group with 1-3 equivalents of formaldehyde (37%) in the presence of an equal or double quantity of formic acid (98-100%) or another hydrogen source, in a reaction inert solvent chosen from halogenated hydrocarbons, e.g. chloroform, or lower alcohols, e.g. methanol or ethanol, lower ketones, e.g. acetone, at reflux temperature of the reaction mixture within 2 to 8 hours, yielding upon the isolation of the product by means of conventional ph-gradient extraction methods (pH 5.0 and pH 9.0) O-methyl-azithromycin A derivatives of formula (I), wherein Ii $R^1=R^4=R^5=H$, $R^2=R^3=CH_3$
Ij $R^1=R^5=H$, $R^2=R^3=R^4=CH_3$
Ik $R^1=R^3=R^5=H$, $R^2=R^4=CH_3$
Il $R^1=H$, $R^2=R^3=R^4=R^5=CH_3$ or B) elimination of the protecting benzoyloxycarbonyl group in 2'- and 3'-positions by hydrogenolysis as described in A), yielding a mixture of 6-O-methyl- (Ie), 6,11-di-O-methyl- (If), 11-O-methyl- (Ig) and 6,11,4"-tri-O-methyl-N-demethylazithromycin A (Ih), which is subjected to reductive N-methylation with formaldehyde (37%) in the presence of formic acid (98-100%) or some other hydrogen source, as described in A), yielding a mixture of 6-O-methyl- (Ii), 6,11-di-O-methyl- (Ij), 11-O-methyl- (Ik) and 6,11,4"-tri-O-methyl-azithromycin A (Il), which is subjected to separation on a silica gel column with the solvent system $CH_2Cl_2/CH_3OH/NH_4OH$ (90:9:0.5), yielding chromatographically homogenous (TLC, the same solvent system) O-methyl derivatives of azithromycin A (Ii) of an $R_f$ 0.346, (Ij) of in $R_f$ 0.393, (Ik) of an $R_f$ 0.428 and (Il) of an $R_f$ 0.456.

Pharmaceutically acceptable addition salts of the compounds of formula (I) are obtainable by reacting O-methyl derivatives of azithromycin A (I) with at least an equimolar quantity of a corresponding organic or inorganic acid, chosen e.g. from hydrogen chloride, hydrogen iodide, sulphuric acid, phosphoric acid, acetic acid, propionic acid, trifluoroacetic acid, maleic acid, citric acid, ethyl succinic acid, succinic acid, methanesulfonic acid, benzenesulfonic acid, p-toluenesulfonic acid, lauryl- sulfonic acid and the like, in a reaction inert solvent. The addition salts are isolated by filtration if they are insoluble in the applied reaction inert solvent, or by precipitation by means of a non-solvent, most often by means of a lyophilization procedure.

O-methyl derivatives of azithromycin A of the formulae (Ii)–(Il) and their pharmaceutically acceptable addition salts have a potent antimicrobial activity. The preliminary antibacterial in vitro activity of 6-O-methyl-azithromycin A (Ii) was determined on a series of gram-positive and gram-negative test bacteria and clinical isolates in comparison with erythromycin A. The assessment was performed by the "tube dilution" method. In the investigation there were used 24-hours cultures in "brain hearth bouillon" of standard strains and freshly isolated strains from a clinical sample. The results are expressed as Minimal Inhibitory Concentration or Bactericidal Concentration (MIC and MBC resp. in /Ag/mL) and represented in Tables 1 and 2, and they show that 6-O-methyl-azithromycin A has a somewhat improved activity on the investigated strains in comparison with erythromycin A.

In Table 3 there are represented in vitro tests of 6-O-methyl- (Ii), 6,11-di-O-methyl- (Ij), 11-O-methyl- (Ik) and 6,11,4''-tri-O-methyl-azithromycin A (Il) in comparison with azithromycin. Minimal Inhibitory Concentrations (MIC; μg/mL) determined on a series of standard bacterial strains show that 6-O-methyl-azithromycin A (Ii) is twice as active on *Bacillus subtilis* NCTC 8241 and *Sarcina lutea* ATCC 9341, and four times as active on *Micrococcus flavus* ATCC 6538 P with respect to azithromycin. A significantly higher activity was also exhibited by 11-O-methyl-azithromycin A (Ik). Namely, the majority of the investigated bacterial strains was 2 to 4 times more sensitive in comparison with the parent antibiotic.

It is a further object of the present invention to provide pharmaceuticals comprising an effective, yet physiologically acceptable dose of the novel compounds of the present invention. Compounds (Ii)–(Il) as well as their pharmaceutically acceptable salts may be used as therapeutical agents in the treatment of human or animal infectious diseases caused by gram-positive bacteria, mycoplasmas or patogenous bacteria, which are sensitive to compounds (Ii)–(Il). Thus, the compounds (Ii)–(Il) and their pharmaceutically acceptable addition salts may be administered orally or parenterally, e.g. in the form of s.c. or i.m. injections, tablets, capsules, powders and the like, formulated in accordance with the conventional pharmaceutical practice.

TABLE 1

Antibacterial in vitro activity of 6-O-methyl-azithromycin A (Ii) in comparison with erythromycin A

| Test Organism | Erythromycin A | | 6-O-methyl-azithromycin A (Ii) | |
|---|---|---|---|---|
| | MIC | MBC | MIC | MBC |
| *Staphilococcus aureus* ATCC 6538-P | 0.2 | 0.8 | 0.2 | 0.4 |
| *Streptococcus faecalis* ATCC-8043 | 0.2 | 0.8 | 0.2 | 0.4 |
| *Sarcina lutea* ATCC-9341 | 0.2 | 0.4 | 0.1 | 0.2 |
| *Escherichia coli* ATCC 10536 | 50 | >50 | 1.6 | 3.2 |
| *Klebsiella pneumoniae* NCTC-10499 | >50 | >50 | 12.5 | 50 |
| *Pseudomonas aeruginosa* NCTC-10490 | >50 | >50 | >50 | >50 |

Substrate: Brain hearth bouillon
Incubation: 24 hours, 37° C.
MIC: Minimal Inhibitory Concentration (μg/mL)
MBC: Minimal Bactericidal Concentration (μg/mL)

TABLE 2

Antibacterial in vitro activity of 6-O-methyl-azithromycin A (Ii) in comparison with erythromycin A against clinical isolates

| Test Organism | Erythromycin A | | 6-O-methyl-azithromycin A (Ii) | |
|---|---|---|---|---|
| | MIC | MBC | MIC | MBC |
| *Staphylococcus aureus* 10099 | 0.1 | 0.2 | 0.05 | 0.1 |
| *Staphylococcus saprophyticus* 3947 | 0.4 | 0.8 | 0.4 | 0.8 |
| *Streptococcus faecalis* 10390 | 0.8 | 3.1 | 0.8 | 3.1 |
| *Staphylococcus aureus* 10097 | 0.1 | 0.4 | 0.05 | 0.4 |
| *Streptococcus pneumoniae* 4050 | 0.1 | 0.4 | 0.025 | 0.1 |
| *Haemophylus influenzae* 4028 | 0.05 | 0.2 | 0.05 | 0.2 |

Substrate: Brain hearth bouillon
Incubation: 24 hours, 37° C.
MIC: Minimal Inhibitory Concentration (μg/mL)
MBC: Minimal Bactericidal Concentration (μg/mL)

TABLE 3

Antibacterial in vitro activity of the novel O-methyl-azithromycin A derivatives in comparison with azithromycin

| Test Strain | MIC (μg/mL) | | | | |
|---|---|---|---|---|---|
| ATCC 6538P | 1.56 | 0.39 | 1.56 | 0.2 | 3.125 |
| *Corynebacterium xerosis* NCTC 9755 | 6.25 | 12.5 | 12.5 | 1.56 | 25.0 |
| ATCC 10240 | 0.39 | 0.79 | 0.78 | 0.1 | 3.125 |
| *Bacillus subtilis* NCTC 8241 | 0.39 | 0.2 | 0.78 | 0.1 | 3.125 |
| *Bacillus pumilus* NCTC 8241 | 0.2 | 0.2 | 0.78 | 0.05 | 3.125 |
| *Bacillus cereus* NCTC 10320 | 0.39 | 0.78 | 1.56 | 0.1 | 3.125 |
| *Sarcina lutea* ATCC 9341 | 0.05 | 0.0125 | 0.05 | 0.0125 | 0.05 |
| *Staphylococcus epidermidis* ATCC 12228 | 0.1 | 0.1 | 1.56 | 0.1 | 3.125 |
| *Staphylococcus faecalis* ATCC 8043 | 0.05 | 0.05 | 0.78 | 0.05 | 0.78 |
| *Pseudomonas aeruginosa* NCTC 10490 | 100.0 | 100.0 | 100.0 | 25.0 | 200.0 |
| *Escherichia coli* ATCC 10536 | 0.78 | 3.125 | 6.25 | 0.78 | 6.25 |

Substrate: Brain hearth Bouillon
Incubation: 24–48 hours, 37° C.
Inocculum; $10^{-5}$–$10^{-6}$ cfu/mL The invention is illustrated by the following Examples.

EXAMPLE 1

2'-0,3'-N-Bis(benzyloxycarbonyl)-N-demethyl-azithromycin (IIb)

Method A

Upon the addition of NAHCO$_3$ (48g) into a solution of azithromycin dehydrate (30 g; 0.038 mole) in 140 mL of dry benzene the reaction mixture was heated under stirring to 55°–60° C., whereupon there were added drop by drop gradually within 1 hour 75 mL (89.63 g; 0.53 mole) of benzyl chloroformate. The reaction mixture was kept stirring at this temperature for 3 hours and left standing overnight at room temperature. The benzene suspension was extracted three times with 150 mL of 0.25N HCl, the benzene solution was dried over CaCl$_2$, filtered, and evaporated at reduced pressure into a thick oil. The obtained residue was added drop-by-drop under thorough stirring into 500 mL of cooled petrolether, the reaction suspension was stirred under cooling for 4 hours, the precipitate was filtered, washed with petroleum ether and dried, yielding 27.5 g (71.6%) of the title product, which upon recrystallization from ether/petroleum ether yielded a product of a m.p. 148°–154° C.

EI-MS m/s 1003 (M$^{30}$).

TLC, CH$_2$Cl$_2$/CH$_3$OH/NH$_4$OH (90:9:0.5) R$_f$0.704.

IR (CHCl$_3$): 3510, 3350, 2960, 1740, 1690, 1605, 1450, 1380, 1330, 1290, 1255, 1160, 1115, 1050, 995 cm$^{-1}$.

$^1$H NMR (CDCl$_3$): 2.301 (3H, 9a-NCH$_3$), 2.844, 2.802 (3H, 3'-NCH$_3$), 3.397 (3H, 3''-OCH$_3$).

$^{13}$C NMR (CDCl$_3$): 177.260 (C-1), 100.115 (C-1'), 95.149 (C-1''), 75.028 (C-6), 74.607 (C-12), 69.415 (C-9), 64.617 (C-10), 36.964 (9a-NCH$_3$) and 26.016 (C-8) ppm.

Method B

Upon the addition of NAHCO$_3$ (22 g) under stirring into a solution of benzyl chloroformate (30 mL; 0.21 mole) in 50 mL of dry benzene, there were added gradually within 3 hours 15 g (0.019 mole) of azithromycin. At the moment of the addition of about ¾ of the total amount of azithromycin, there was added a further quantity of 15 mL (0.106 mole) of benzyl chloroformate. The reaction mixture was kept under stirring for 24 hours at room temperature, filtered, whereupon the filtrate was extracted three times with 150 mL of 0.25N HCl, dried over MGSO$_4$ and evaporated at reduced pressure. Upon the addition of petroleum ether the crude 2'-O,3'-N-bis-(benzyloxycarbonyl)-N-demethyl-azithromycin A was precipitated, the obtained precipitate was filtered and immediately suspended under stirring in 50 mL of cold ether. The reaction suspension was stirred at room temperature for 1 hour, the precipitate was filtered and dried, yielding 8.67 g (43.09%) of a homogeneous product (TLC) of identical physical-chemical characteristics as cited above in Method A.

EXAMPLE 2

O-Methylation of 2'-O,3'-N-bis(benzyloxycarbonyl)-N-demethyl-azithromycin A (Ia), (Ib), (Ic) and (Id)

Method A

Upon the addition of methyl iodide (6 mL; 0.106 mole) into a solution of the product of Example 1 (6 g; 0.006 mole) in 64 mL of dimethyl sulfoxide and tetrahydrofurane (1:1), there were ;added methyl iodide (6.6 mi; 0.106 mole) and then, gradually within 4 hours at room temperature 2.4 g (approx. 0.06 mole) of NaH (55–60%) in oil. The reaction suspension was stirred for further 5 hours, left standing overnight, poured into a saturated NaCl solution (100 mi), and extracted twice with 100 mL of ethyl acetate. The combined organic extracts were washed three times with 100 mL of saturated NaCl solution, dried over K$_2$CO$_3$, and evaporated, yielding 6.35 g of a crude product, which was subjected to hydrogenolysis in accordance with the process described in Example 9 or, optionally, to purification by means of chromatography on a silica gel column (Silica gel 60, Merck Co., 70–230 mesh), using the solvent system CH$_2$C$_2$/CH$_3$OH/NH$_4$OH (90:9:0.5).

From 1.5 g of the crude product there were obtained, upon the concentration and evaporation of the fractions of R$_f$ 0.881 (TLC; identical solvent system), 0.12 g of the chromatographically pure 2'-O,3'-N-bis(benzyloxycarbonyl)-N-demethyl-6,11,4''-tri-O-methyl-azithromycin A (Id):

$^1$H NMR (CDCl$_3$): 2.246 (3H, 9a-NCH$_3$), 2.831, 2.798 (3H, 3'-NCH$_3$), 3.367 (3H, 3''-OCH$_3$), 3.305 (3H, 6-OMe), 3.465 (3H, 4''-OCH$_3$), and 3.485 (3H, 11-OCH$_3$) ppm.

13C NMR (CDCl$_3$): 176.975 (C-1), 69.920 (C-9), 35.967 (9a-NCH$_3$), 79.1 (C-6). 52.8 (6-OCH$_3$), 89.0 (C-11), 62.0 (11-OCH$_3$), 87.357 (C-4''), 61.131 (4''-OCH$_3$), 49.176 and 49.526 (3''-OCH$_3$) and 36.457 (3'-NCH$_3$) ppm.

Upon the combination and evaporation of the fractions of R$_f$ 0.843, 0.32 g of the chromatographycally pure 2'-O,3'-N-bis(benzyloxycarbonyl)-N-demethyl-11-O-methyl-azithromycin A (Ic) were obtained:

EI-MS m/s 1016 (M+).

$^1$H NMR (CDCl$_3$): 2.239 (3H, 9a-NCH$_3$), 2.805, 2.847 (3H, 3'-NCH$_3$), 3.374 (3H, 3''-OCH$_3$), and 3.573 (3H, 11-OCH$_3$) ppm.

Upon the evaporation of the fractions of R$_f$ 0.811, 0.316g of 2'-O,3'-N-bis(benzyloxycarbonyl)-N-demethyl-6,11-di-O-methyl-azithromycin A (Ib) were obtained:

IR (CHCl$_3$): 3570, 3490, 1740, 1690, 1455, 1380, 1330, 1295, 1260, 1200, 1160, 1120, 1095, 1055, 1005, 990, 980 cm$^{-1}$.

$^1$H NMR (CDCl$_3$): 2.292 (3H, 9a-NCH$_3$), 2.838, 2.795 (3H, 3'-NCH$_3$), 3.380 (6H, 6-OCH$_3$ and 3''-OCH$_3$) and 3.488 (3H, 11-OCH$_3$) ppm.

$^{13}$C NMR (CDCl$_3$): 177.939 (C-1), 69.471 (C-9), 35.271 (9a-NCH$_3$), 88.994 (C-11), 52.892 (6-OCH$_3$), 61.09 (11-OCH$_3$), 36.851 (3'-NCH$_3$), and 49.549, 49.154 (3''-OCH$_3$) ppm.

Upon concentration and evaporation to dryness of the fractions of R$_f$ 0.661, 0.384 g of 2'-O,3'-N-bis(benzyloxycarbonyl)-N-demethyl-6-O-methyl-azithromycin A (Ia) were obtained:

EI-MS m/s 1016 (M+).

IR (CHCl$_3$): 3570, 3500, 2960, 2920, 1740, 1690, 1450, 1380, 1325, 1290, 1255, 1200, 1160, 1120, 1050, 995 cm$^{-1}$.

$^1$H NMR (CDCl$_3$): 2.288 (3H, 9a-NCH$_3$), 2.805, 2.847 (3H, 3'-NCH$_3$), 3.380 (6H, 6-OCH$_3$ and 3''-OCH$_3$) ppm.

$^{13}$C NMR (CDCl$_3$): 177.764 (C-1), 69.850 (C-9), 34.851 (9a-NCH$_3$), 78.106 (C-6), 74.661 (C-11), 73.873 (C-12), and 52.822 (6-OCH$_3$) ppm.

Method B

Into a solution of the product of Example 1 (6 g) in 60 mL of dimethyl sulfoxide and tetrahydrofurane (1:1), there was added, under stirring, gradually within 2 hours at a temperature of 0°–5° C. methyl iodide (3 mL) and 2.1 g of NaH (55–60%). The reaction mixture was stirred for 1 hour at 0°–5° C., the suspension was poured on a saturated NaCl solution and extracted with ethyl acetate. The organic extracts were washed with a saturated NaCl solution, dried over K$_2$CO$_3$, and evaporated to dryness at reduced pressure. The obtained product (2 g) was subjected to purification by means of chromatography on a silica gel column, using the solvent system CH$_2$Cl$_2$/CH$_3$OH/NH$_4$OH (90:9:1.5) and yielding 0.89 g of 6-O-methyl derivative (Ia), 0.11 g of 6,11-di-O-methyl derivative (Ib) and 0.48 g of 11-O-methyl derivative (Ic).

Method C

Upon the addition of methyl iodide (6 mL) into a solution of the product of Example 1 (6 g) in 60 mL of N,N-dimethylformamide, there were added, under stirring, gradually within 2 hours at room temperature 2.4 g of NaH (55–60%). The reaction mixture was stirred for further 2 hours at said temperature and left overnight. Upon the isolation of the product in accordance with the procedure described in Method A, there were obtained 4.54 g of a mixture of 6,11-di-O-methyl derivative (Ib) and 6,11,4''-tri-O-methyl derivative (Id). This mixture was subjected to hydrogenolysis in methanol (60 mL) in the presence of a NaOAc/HOAc buffer (pH 5) and palladium-on-carbon (2g; 5%) as catalyst, according to the procedure described in Example 3.

Upon the isolation of the product and evaporation of the solvent at pH 9.0 there was isolated a mixture (2.33g) of 6,11-di-O-methyl-N-demethyl-azithromycin A (If) of $R_f$ 0.220 and 6,11,4''-tri-O-methyl-N-demethyl-azithromycin A (Ih) of $R_f$ 0.263, which upon separation on a silica gel column in the solvent system $CH_2Cl_3/CH_3OH/NH_4OH$ (90:9:1), yielded a chromatographically homogeneous product (If) and (Ih).

EXAMPLE 3

6-O-Methyl-N-demethyl-azithromycin A (Ie)

2.0 g (0.002 mole) of 2'-O,3'-N-bis(benzyl-oxycarbonyl)-N-demethyl-6-O-methyl-azithromycin A (Ia) were dissolved in 30 mL of ethanol. 10 mL of water, which contained 0.185 mL of acetic acid and 0.3 g of sodium acetate (pH 5) and 0.7 g of palladiumon-carbon (10%) was charged into the solution. The reaction mixture was stirred under hydrogen pressure (10 bar) for 10 hours, the catalyst was filtered and evaporated to dryness. The residue was dissolved in $CHCl_3$ (30 mL) and upon the addition of water (30 mL) and adjustment of the pH of the reaction mixture with 1N HCl to 5.0, the layers were separated and the aqueous layer was extracted twice with $CHCl_3$ (each time with 15 mL).

To the reaction mixture $CHCl_3$ (30 mL) was added, the pH was adjusted to 9.0 under stirring with 2N NAOH, the layers were separated, and the aqueous layer was again extracted twice with $CHCl_3$ (each time with 15 mL). The combined organic extracts (pH 9.0) were dried over $K_2 CO_3$, filtered and evaporated to yield 1.03 g (70%) of the title product:

EI-MS m/s 748.
TLC, $R_f$ 0.182.
IR ($CHCl_3$): 3670, 3500, 2960, 2920, 1725, 1460, 1375, 1345, 1320, 1280, 1260, 1165, 1120, 1085, 1045, 1010. 995, 900 cm$^{-1}$.
$^1$H NMR ($CDCl_3$): 2.278 (3H, 9a-NCH$_3$), 2.406 (3H, 3'-NCH$_3$), 3.312 (3H, 3''-OCH$_3$), 3.384 (3H, 6-OCH$_3$) ppm.

EXAMPLE 4

6,11-Di-O-Methyl-N-demethyl-azithromycin A (If)

In accordance with the procedure of Example 3, from 0.165 g (0.16 mole) of 2'-O,3'-N-bis-(benzyloxycarbonyl)-N-demethyl-6,11-di-O-methyl-azithromycin A (Ib) by means of hydrogenolysis with palladium-on-carbon (10%) in ethanol in the presence of the buffer sodium acetate/acetic acid (pH 5.0), there were obtained 0.093 g (76,2%) of the chromatographically homogeneous title product; m.p. 95°–98° C.

EI-MS m/s 762.
TLC, $R_f$ 0.331.
$^1$H NMR ($CDCl_3$): 2.265 (3H, 9a-CH$_3$), 2.422, (3H, 3'-NCH$_3$), 3.312 (3H, 3''-OCH$_3$), 3.374 (3H, 6-OCH$_3$) and 3.521 (3H, 11-OCH$_3$) ppm.
$^{13}$C NMR ($CDCl_3$): 177.7 (C-1), 65.9 (C-9), 36.8 (9a-NCH$_3$), 79.3 (C-6), 88.9 (C-11), 52.7 (6-OCH$_3$), 62.0 (11-OCH$_3$), 33.1 (3'-NCH$_3$), and 49.7 (3''-OCH$_3$) ppm.

EXAMPLE 5

11-O-Methyl-N-demethyl-azithromycin A (Ig)

In accordance with the procedure of Example 3, from 0.250 g (0.246 mmole) of 2'-O,3'-N-bis(benzyloxycarbonyl)-N-demethyl-11-O-methyl-azithromycin A (Ic) by means of hydrogenolysis with palladium-on-carbon (10%) in methanol in the presence of the buffer sodium acetate/acetic acid (pH 5.0), there were obtained 0.168 g (89,5%) of 11-O-methyl-N-demethyl-azithromycin A (Ig):

TLC, $R_f$ 0.244.
IR ($CDCl_3$): 3500, 2970, 2940, 1736, 1460, 1380, 1165 cm$^{-1}$.
$^1$H NMR ($CDCl_3$): 2.44 (3H, 9a-NCH$_3$), 2.458, (3H, 3'-NCH$_3$), 3.336 (3H, 3''-OCH$_3$) and 3.590 (3H, 11-OCH$_3$) ppm.
$^{13}$C NMR ($CDCl_3$): 177.6 (C-1), 70.7 (C-9), 35.8 (9a-NCH$_3$), 74.4 (C-6), 85.0 (C-11), 62.7 (11-OCH$_3$), 36.7 (3'-NCH$_3$), and 49.4 (3''-OCH$_3$) ppm.

EXAMPLE 6

6-O-Methyl-azithromycin A (Ii)

Method A

Into a solution of 0.78 g (0.00104 mole) of 6-O-Methyl-N-demethyl-azithromycin A (Ie) in $CHCl_3$ (50 mL) there were added 0.085 mL (0.00113 mole) of formaldehyde (37%) and 0.078 mL (0.00203 mole) of formic acid (98–100%). The reaction mixture was stirred under reflux for 8 hours, cooled to room temperature, and poured onto 50 mL of water. Upon the adjustment of the pH of the reaction mixture with 1N HCl to 5.0, the layers were separated and the aqueous layer was extracted twice with $CHCl_3$ (each time with 20 mL). To the aqueous portion $CHCl_3$ (20 mL) was added, the pH was adjusted to 9.0 under stirring with 2N NAOH, the layers were separated, and the aqueous layer was again extracted twice with $CHCl_3$ (each time with 20 mL). The combined $CHCl_3$ extracts (pH 9.0) were dried over $K_2 CO_3$ and evaporated to yield 0.495 g (62,74%) of the title product, which was optionally purified by chromatography on a silica gel column, using the solvent system $CH_2Cl_2/CH_3OH/NH_4OH$ (90:9:0.5) and yielding chromatographically homogeneous (Ii), m.p. 103°–109° C.

EI-MS m/s 762.
TLC, $R_f$ 0.346.
IR (KBr): 3500, 2980, 2940, 1740, 1462, 1385, 1330, 1280, 1260, 1170, 1112, 1059, 1018, and 1055 cm$^{-1}$.
$^1$H NMR ($CDCl_3$): 2.300 (3H, 9a-NCH$_3$), 2.316 (6H, 3'-N(CH$_3$)$_2$), 3.333 (3H, 3''-OCH$_3$) and 3.384 (3H, 6-OCH$_3$) ppm.
$^{13}$C NMR ($CDCl_3$): 177.540 (C-1), 68.850 (C-9), 36.8 (9a-NCH$_3$), 79.2 (C-6), 52.822 (6-OCH$_3$), 61.627 (C-10), 40.350 (3'-N(CH$_3$)$_2$) and 49.457 (3''-OCH$_3$) ppm.

Biological activity: 1 mg contains 754 μg of azithromycin.

Method B

Into a solution of 0.5 g (0.668 mmole) of 6-O-methyl-N-demethyl-azithromycin A in acetone (30 mL) there were added 0.128 mL (1.71 mmole) of formaldehyde (37%) and 0.118 mL (3.06 mmole) of formic acid (98–100%), and it was refluxed under stirring for 2 hours. The reaction mixture was cooled to room temperature and acetone was evaporated to yield a thick syrup and upon addition of 20 mL of water the product was isolated by means of gradient pH extraction by means of methylene chloride as described in Method A). Yield: 0.46 g (90.3%).

EXAMPLE 7

6,11-Di-O-Methyl-azithromycin A

In accordance with the procedure of Example 6, from 0.49 g (6.43 mmole) of 6,11-di-O-methyl-N-demethylazithromycin A (If) by means of reductive N-methylation with formaldehyde (37%; 0.083 mL) in the presence of formic acid (98–100%), there were obtained 0.46 g (92,3%) of the title product:

EI-MS m/s 776 (M+).

TLC, $R_f$ 0.391.

$^1$H NMR (CDCl$_3$): 2.295 (3H, 9a-NCH$_3$), 2.316 (6H, 3'-N(CH$_3$)$_2$), 3.321 (3H, 3"-OCH$_3$) 3.38 (3H, 6-OCH$_3$) and 3.524 (3H, 11-OCH$_3$) ppm.

$^{13}$C NMR (CDCl$_3$): 177.540 (C-1), 68.237 (C-9), 36.739 (9a-NCH$_3$), 88.112 (C-11), 52.653 (6-OCH$_3$) and 61.852 (11-OCH$_3$) ppm.

EXAMPLE 8

11-O-Methyl-azithromycin A (Ik)

In accordance with the procedure of Example 6, from 0.32 g (0.43 mmole) of 11-O-methyl-N-demethylazithromycin A (Ig) by means of reductive methylation with formaldehyde (37%) in the presence of formic acid (98–100%), there were obtained 0.238 g (72,44%) of the title 11-O-methyl derivative (Ik):

EI-MS m/s 762 (M+).

TLC, $R_f$ 0.428.

IR (KBr): 3510,2975,2940,1738,1460,1350,1165,1054cm$^{-1}$.

$^1$H NMR (CDCl$_3$): 2.246 (3H, 9a-NCH$_3$), 2.307 (6H, 3'-N(CH$_3$)$_2$), 3.352 (3 H, 3"-OCH$_3$) and 3.591 (3H, 11-OCH$_3$) ppm.

EXAMPLE 9

6-O-Methyl-azithromycin A (Ii), 6,11-di-O-methyl-azithromycin A (Ij), 11-O-methyl-azithro- mycin A (Ik) and 6,11,4"-tri-O-methyl-azithromycin A (Il)

1) Into a solution of 2.16 g of the crude product of Example 2 in 30 mL of ethanol, there were added 10 mL of water containing 0.185 mL of acetic acid and 0.3 g of sodium acetate and 0.7 g of palladium-on-carbon (10%), whereupon the reaction mixture was subjected to hydrolysis, as described in Example 3. At a pH of 9.0 there were obtained 0.98 g of a mixture of 6-O-methyl- (Ie), 6,11-di-O-methyl- (If), 11-O-methyl- (Ig), and 6,11,4"-tri-O-methyl-N- demethyl-azithromycin A (Ih).

2) Upon the dissolving of 0.98 g of the mixture obtained as described in (1), in CHCl$_3$ (50 mL), there were added 0.106 mL of formaldehyde (37%) and 0.096 mL of formic acid (98–100%) and it was subjected to N-methylation as described in Example 6. At a pH of 9.0 there were isolated 0.537 g of a mixture, which was subjected to chromatography on a silica gel column (Silica gel 60, Merck Co., 70–230 mesh), using the solvent system CH$_2$Cl$_2$/CH$_3$OH/NH$_4$OH (90:9:1.5), and yielding 0.238 g of a chromatographically homogeneous (Ii) of $R_f$ 0.346, 0.065 g of (Ij) of $R_f$ 0.391, 0.105 g (Ik) of $R_f$ 0.428 and 0.094 g (Il) of $R_f$ 0.456.

EXAMPLE 10

6,11,4"'-Tri-O-Methyl-N-demethyl-azithromycin A (Ih)

In accordance with the procedure of Example 3, from 3.35 g (3.21 mmole) of 2'-0,3'-N-bis-(benzyloxycarbonyl)-N-demethyl-6,11,4"-tri-O-methyl-azithromycin A (Id) by means of hydrogenolysis with palladium-on-carbon (10%; 1 g) in ethanol (50 mL) in the presence of the buffer sodium acetate/acetic acid (pH 5.0), there were obtained 1.41 g (56,7%) of the title product, which was optionally subjected to chromatography on a silica gel column using the solvent system CH$_2$Cl$_2$/CH$_3$OH/NH$_4$OH (90:9:0.5), and yielding a TLC homogeneous product (Ih):

EI-MS m/s 775.

TLC, $R_f$ 0.263.

$^1$H NMR (CDCl$_3$): 2.262 (3H, 9a-NCH$_3$) , 2.393 (3H, 3'-NCH$_3$), 3.308 (6H, 3"-OCH$_3$ and 6-OCH$_3$), 3.475 (4"-OCH$_3$) and 3.521 (11-OCH$_3$) ppm.

$^{13}$C NMR (CDCl$_3$): 175.0 (C-1), 64.8 (C-9), 79.8 (C-6), 50.6 (6-OCH$_3$) 86.1 (C-11), 59.1 (11-OCH$_3$), 87.7 (C-4") and 60.9 (4"-OCH$_3$) ppm.

EXAMPLE 11

6,11,4"'Tri-O-Methyl-azithromycin A (Il)

In accordance with the procedure of Example 6, from 1.2 g (1.55 mmole) of 6,11,4"-tri-O-methyl-N-demethyl-azithromycin A (Ih), 0.131 mL of formaldehyde (37%; 1.71 mmole) and 0.121 mL (3.15 mmole) of formic acid (98–100%), there were obtained 0.75 g (64,4%) of the title product.

EI-MS m/s 789.

TLC, $R_f$ 0.456. $^1$H NMR (CDCl$_3$): 2.216 (3H, 9a-NCH$_3$) , 2.311 (6H, 3'-N(CH$_3$)$_2$), 3.321 (3H, 3"-OCH$_3$), 3.302 (6-OCH$_3$), 3.482 (4"-OCH$_3$) and 3.521 (11-OCH$_3$) ppm.

$^{13}$C NMR (CDCl$_3$): 177.859 (C-1), 68.6 (C-9), 36.8 (9a-NCH$_3$), 80.7 (C-6), 51.0 (6-OCH$_3$) 89.0 (C-11), 62.0 (11-OCH$_3$), 87.3 (C-4") and 61.3 (4"-OCH$_3$) ppm.

What is claimed is:

1. O-methyl derivative of azithromycin A of the formula (I)

wherein
$R^1 = R^4 = R^5 = H$, $R^2 = R^3 = CH_3$ or
$R^1 = R^3 = R^5 = H$, $R^2 = R^4 = CH_3$ or a pharmaceutically acceptable addition salt with inorganic or organic acid.

2. The derivative of azithromycin A as claimed in claim 1, characterized in that $R^1$, $R^4$, and $R^5$ are identical and stand for hydrogen, whereas $R^2$ and $R^3$ stand for CH$_3$.

3. The derivative of azithromycin A as claimed in claim 1, characterized in that $R^1$, $R^3$, and $R^5$ are identical and stand for hydrogen, whereas $R^2$ and $R^4$ stand for CH$_3$.

4. A method for treating a bacterial infection in a mammal, which comprises administering to a mammal having said infection an antibacterially and pharmaceutically effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 5,250,518
DATED : October 5, 1993
INVENTOR(S) : Kobrehel, et al.

It is certified that error appears in the above-identified patent and that said Letters Patent is hereby corrected as shown below:

Column 1, line 23, please cancel "C-9(S) and C-9(R) ketones" and replace with ---C-9 ketone---.

Column 1, line 25, please cancel "C-9(R) amines" and replace with ---C-9(R) and C-9(S) amines---.

Column 6, Table 3, above the line

"ATCC 6538 P      1, 56    0.39     1,56     0,2      3,125"
please insert the following:

(IIa)    (Ii)    (Ij)    (Ik)    (Il)
Staphylococcus aureus

Column 6, Table 3, above the line that recites:
"ATCC 10240" please insert ---Micrococcus flavus---.

Signed and Sealed this

Twelfth Day of July, 1994

Attest:

BRUCE LEHMAN

Attesting Officer       Commissioner of Patents and Trademarks